(12) United States Patent
Gharibian (10) Patent No.: US 8,052,339 B2
(45) Date of Patent: Nov. 8, 2011

(54) OPERATING ROOM UNIVERSAL DISPOSABLE CAMERA COVER AND ADAPTER SYSTEM

(76) Inventor: Noel Gharibian, Glendale, CA (US)

( * ) Notice: Subject to any disclaimer, the term of this patent is extended or adjusted under 35 U.S.C. 154(b) by 0 days.

(21) Appl. No.: 12/633,754

(22) Filed: Dec. 8, 2009

(65) Prior Publication Data
US 2011/0135295 A1 Jun. 9, 2011

(51) Int. Cl.
G03B 17/00 (2006.01)
G03B 11/00 (2006.01)

(52) U.S. Cl. ........................ 396/448; 396/544

(58) Field of Classification Search .............. 396/448, 396/544; 348/72, 75, 373; 600/112, 122, 600/249; 16/906
See application file for complete search history.

(56) References Cited

U.S. PATENT DOCUMENTS

| | | |
|---|---|---|
| 4,605,124 A | 8/1986 | Sandel et al. |
| 4,844,252 A | 7/1989 | Barron et al. |
| 4,878,156 A | 10/1989 | Hallings et al. |
| 4,974,288 A | 12/1990 | Reasner |
| 4,976,299 A | 12/1990 | Bickelman |
| 5,036,446 A | 7/1991 | Quintanilla et al. |
| 5,065,296 A | 11/1991 | Cude et al. |
| 5,156,456 A | 10/1992 | Hoftman et al. |
| 5,429,142 A | 7/1995 | Szabo et al. |
| 5,498,230 A | 3/1996 | Adair |
| 5,576,781 A | 11/1996 | Deleeuw |
| 5,697,123 A | 12/1997 | Gharibian et al. |
| 5,709,465 A | 1/1998 | Lanzone |
| 5,803,905 A | 9/1998 | Allred et al. |
| 5,971,916 A | 10/1999 | Koren |
| 6,346,073 B1 * | 2/2002 | Thompson ............... 600/112 |
| 6,633,328 B1 | 10/2003 | Byrd et al. |
| 6,692,141 B2 | 2/2004 | Jesurun et al. |
| 6,715,904 B2 * | 4/2004 | Naughton ............... 362/399 |
| 6,909,465 B2 | 6/2005 | Liang |
| 2008/0139881 A1 * | 6/2008 | Cover et al. ............. 600/103 |

* cited by examiner

Primary Examiner — W. B. Perkey
Assistant Examiner — Minh Phan
(74) Attorney, Agent, or Firm — Patent Law Agency, LLC; Peter Ganjian (57) ABSTRACT

A surgical room camera replacement cover assembly comprising a universal adapter interface unit and substantially rigid, disposable, universal camera cover detachably coupled with the universal adapter interface unit.

2 Claims, 13 Drawing Sheets

OPERATING ROOM UNIVERSAL DISPOSABLE CAMERA COVER AND ADAPTER SYSTEM

BACKGROUND OF THE INVENTION

1. Field of the Invention

This invention relates to camera covers, and more specifically, to universal and disposable sterile replacement camera covers that may be used in sterile environments such as an operating room.

2. Description of Related Art

Conventional surgical cameras mounted on surgical light assemblies are well-known and have been in use for a number of years. FIGS. 1A to 1D are illustrations of an exemplary surgical camera mounted on a surgical light assembly, including an Original Equipment Manufacturer (OEM) camera cover. It should be noted that FIGS. 1A to 1D illustrate a very specific surgical camera with a corresponding or matching surgical camera cover that is made specifically for the illustrated surgical camera to exactly match and cover the shown surgical camera. In fact, all existing surgical light assemblies, their associated camera equipment, and their camera cover mounted thereon are unique, specifically manufactured by competing companies and are not interchangeable. Accordingly, the FIGS. 1A to 1D are merely provided for illustrative purposes and for better understanding of the present invention and should not be limiting to the specific surgical light, surgical camera and its correspondingly matching camera cover illustrated.

As illustrated in FIGS. 1A to 1D, an exemplary surgical light assembly 100 may include a surgical light camera 102. The surgical light camera 102 typically includes a camera body 104, a lens 106, and a connection section 108 that connects to the surgical light 100. In general, the connection section 108 of the surgical light camera 102 includes a fastening mechanism 110 that allows coupling of a uniquely manufactured, correspondingly matching OEM camera cover 112 onto the surgical light camera 102.

Figure 1A:
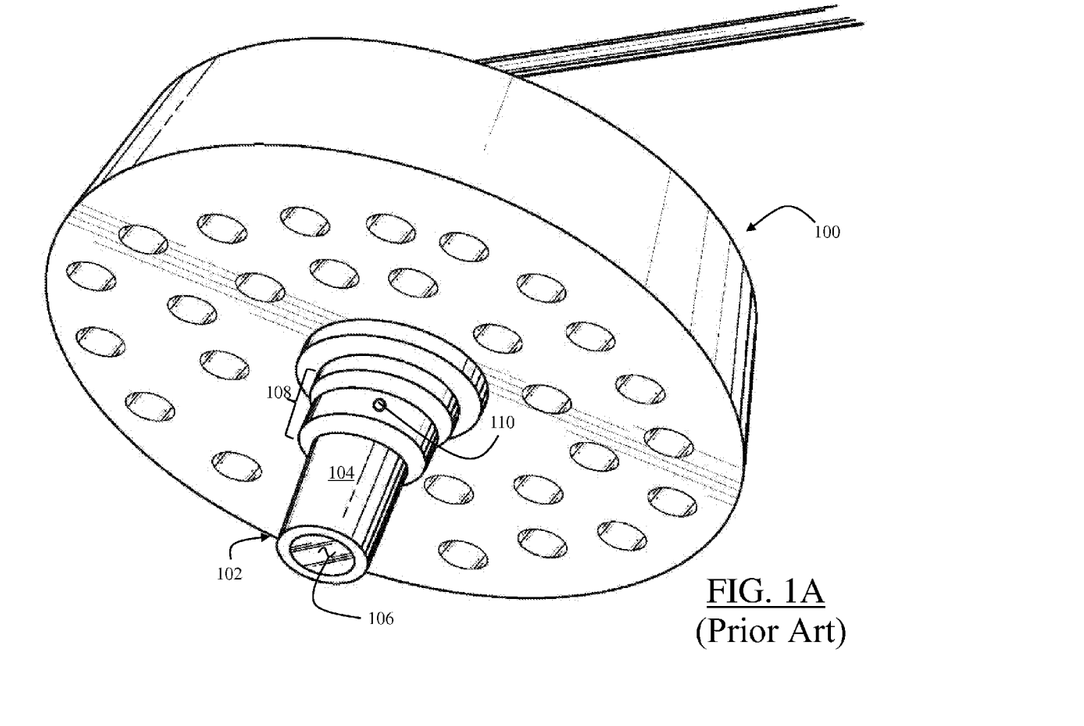
FIGS. 1A to 1D are illustrations of an exemplary surgical camera mounted on a surgical light assembly, including an Original Equipment Manufacturer (OEM) camera cover.
Figure 1B:
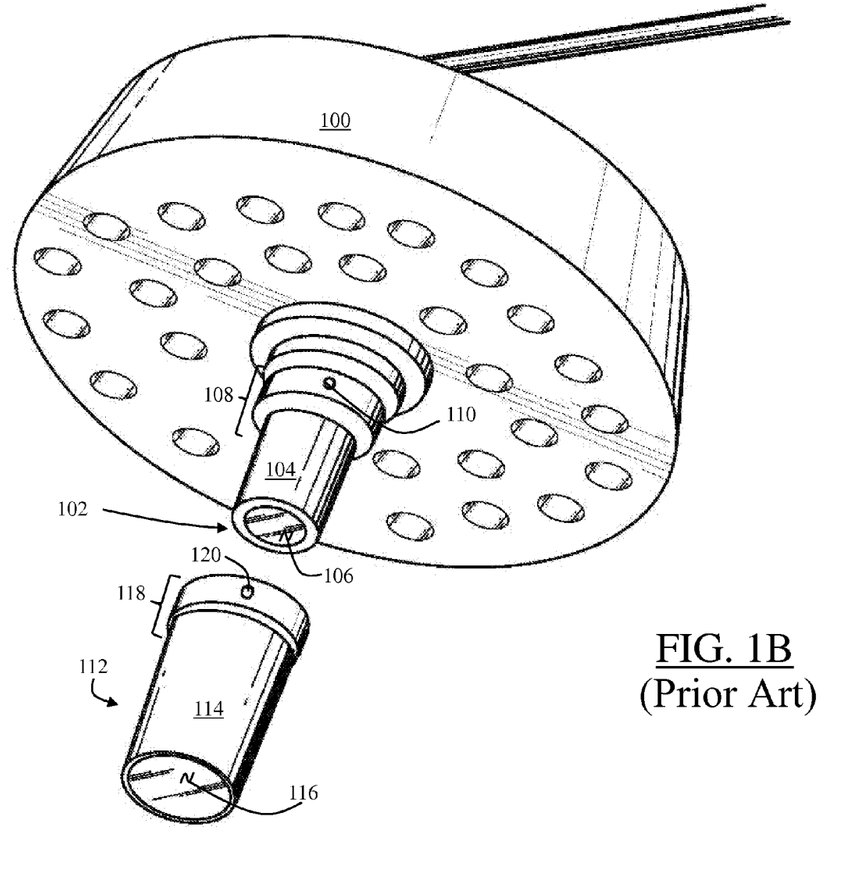

As best illustrated in FIG. 1B, the OEM camera cover 112 is typically comprised of a cover body 114, a lens cover 116, and an upper section 118 that includes a mounting mechanism 120 that detachably couples the OEM camera cover 112 onto a correspondingly matching surgical light camera 102. More specifically, the upper section 118 of the OEM camera cover 112 with its mounting mechanism 120 couples with the connection section 108 of the surgical light camera 102 with its complementary (i.e., corresponding) fastening mechanism 110.

Figure 1C:
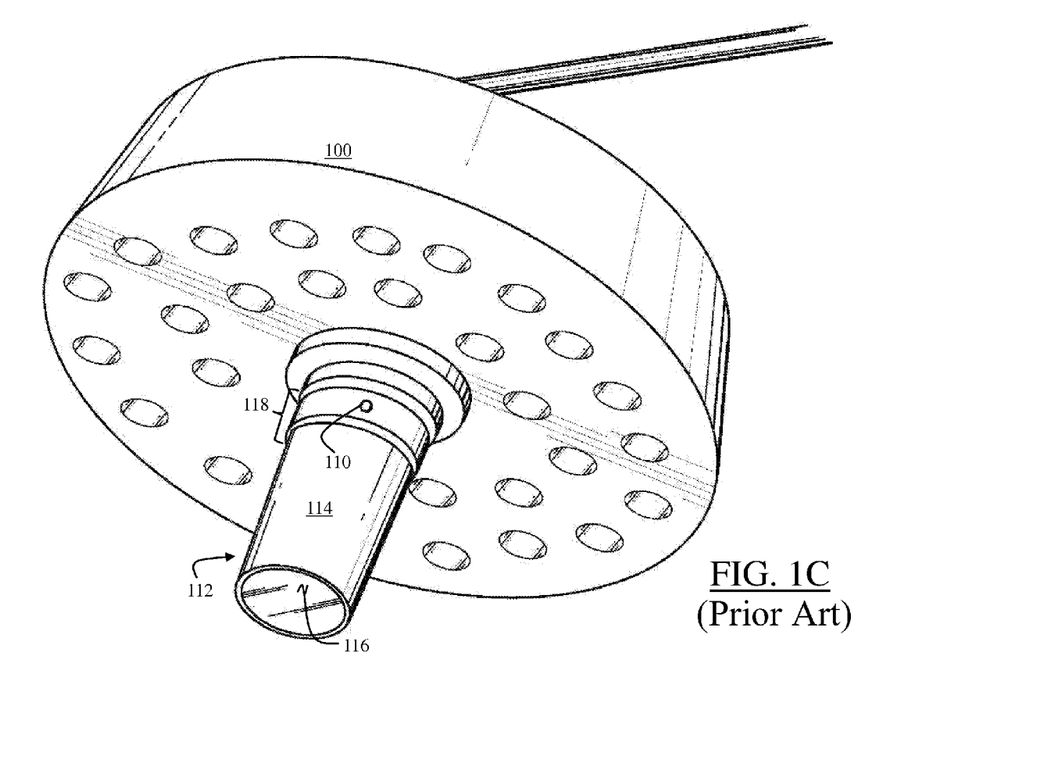
Figure 1D:
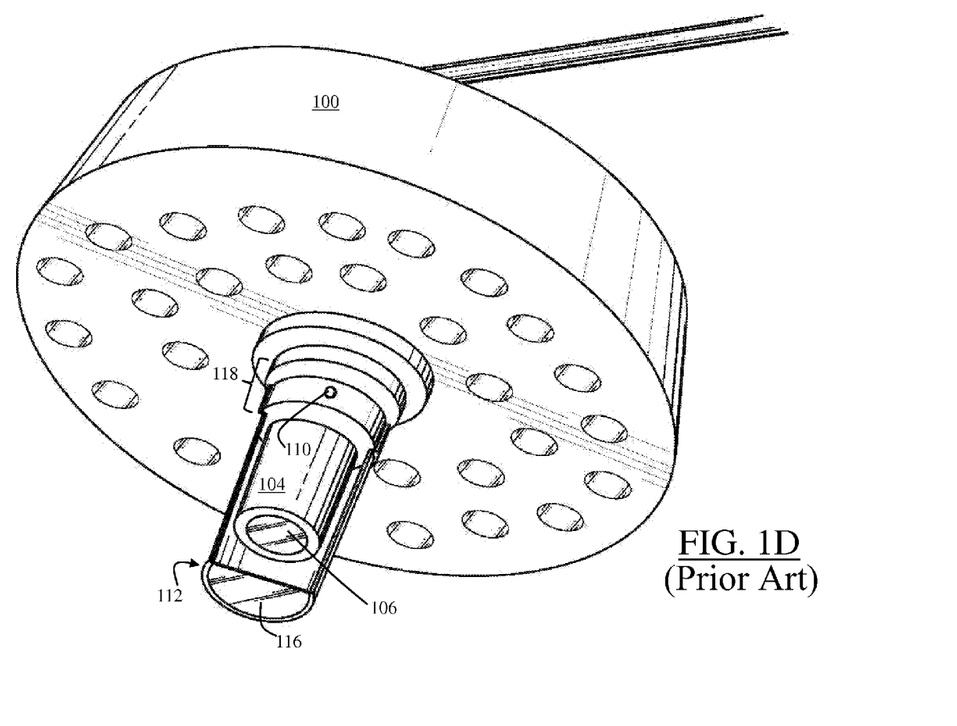

As best illustrated in FIGS. 1C and 1D, in this particular instance, the fastening mechanism 110 of the connection section 108 of the camera 102 is an exemplary biased button that may be biased outward by a spring. On the other hand, the correspondingly matching (i.e., complementary) mounting mechanism 120 of the upper section 118 of the OEM camera cover 112 is an exemplary aperture that receives the fastening mechanism (or biased button) 110 of the OEM camera cover 112, when the OEM camera cover 112 is fully installed. That is, to detachably mount the OEM camera cover 112 onto the surgical light camera 102, the biasing button 110 of the surgical light camera 102 is inserted and locked within the aperture 120.

Regrettably, surgical camera covers, including those illustrated in FIGS. 1A to 1D suffer from obvious disadvantages in that they are not disposable and they are not universal. There are a few disposable accessories that are placed on or drape over an OEM surgical camera cover itself, but these accessories are not rigid and are uniquely and specifically manufactured for a specifically corresponding OEM camera cover, and most are of soft type. Obviously, soft type OEM camera covers do not provide the same level of physical protection for the surgical room camera or the OEM camera cover itself as do the rigid OEM covers and therefore, rigid covers such as the cover 112 are preferred. That is, soft covers must incorporate a viewing area that must always be aligned with the lens of the camera, due to the soft nature of the soft type OEM camera covers, a user may accidentally mishandle and touch the camera or pull the soft cover, which may jeopardize the viewing area of the camera lens or the camera itself.

Nonetheless, as illustrated, rigid OEM operating room camera covers provide a protective, sterilized covering for the more expensive and costly surgical room camera equipment that is mounted onto the surgical light assembly. The rigid OEM camera covers provide a sterile grip section (e.g., the body 114) for maneuvering the camera to different orientations without contacting or grabbing the actual camera equipment. The camera cover is generally dismounted from the camera and the surgical light assembly, and put through a rigorous, time consuming, and costly sterilization procedure after every surgery, enabling the reuse of the actual camera equipment. The camera covers may be considered as a part of the sterile field (or sterile zone) of an operating room.

As stated above, surgical light assemblies, the associated camera equipment, and the camera cover mounted thereon are unique, specifically manufactured by competing companies and are not interchangeable. Accordingly, a hospital having multiple operating rooms may have multiple surgical light assemblies (including the uniquely associated mounted camera and cover) from multiple manufacturing companies, none of which can be interchanged for use. Therefore, for a busy hospital, the constant and continuous use of the operating room is not possible because after every surgery the unique camera cover used must be dismounted and put through the time consuming sterilization procedure, creating a bottleneck effect that impedes the turn-around time for preparation and reuse of the operating room. (Of course, it is assumed that sufficient numbers of sterilization equipments are available to timely handle sterilizing of camera covers and other surgical equipment.)

To overcome the problem associated with the bottleneck effect caused by the sterilizing the uniquely manufacture camera covers, hospitals can order multiple camera covers from different manufacturers. However, this would be impractical in terms of purchasing costs, storage, inventory, and maintenance of the covers. Further, the addition of more camera covers does not obviate or relieve the requirement for their sterilization, but compounds it. Instead of sterilizing a single camera cover, the hospital would have to sterilize multiple camera covers. Other options include the use of disposable accessories, but as mentioned above, these accessories are also uniquely and specifically manufactured for a specific camera cover, are not interchangeable, are very costly, and most are of soft type, which makes it difficult to grip and maneuver the camera during a surgical procedure.

Accordingly, in light of the current state of the relevant art and the drawbacks to current camera covers, a need exists for a sterile replacement camera cover that is disposable, rigid, and universal that may be used with all types of cameras.

BRIEF SUMMARY OF THE INVENTION

One exemplary aspect of the present invention provides a surgical room camera replacement cover assembly, comprising:

a universal adapter interface unit; and a substantially rigid, disposable, universal camera cover detachably coupled with the universal adapter interface unit.

One exemplary optional aspect of the present invention provides a surgical room camera cover replacement assembly, wherein:

the universal adapter interface unit includes:

a first section that is specifically configured to detachably couple with a particular surgical light fixture; and a second section that is configured to universally, detachably couple with the substantially rigid, disposable, universal camera cover.

Another exemplary optional aspect of the present invention provides a surgical room camera cover replacement assembly, wherein The surgical room camera cover replacement assembly as set forth in claim 2, wherein:

the first section includes a fastener that detachably couples with an associated fastener of the particular surgical light fixture; and the second section includes a universal fastener that detachably couples with the substantially rigid, disposable, universal camera cover.

Still another exemplary optional aspect of the present invention provides a surgical room camera cover replacement assembly, wherein:

the substantially rigid, disposable, universal camera cover includes:

a viewing section that provides a view of an operative field for a camera equipment;

a body that houses and provides a sterile, protective covering for the camera equipment;

a barrier that limits a grip of a user to within a sterile field; and a universal coupling section that couples the substantially rigid, disposable, universal camera cover with a second section of the universal adapter interface unit that includes a, universal fastener.

Such stated advantages of the invention are only examples and should not be construed as limiting the present invention. These and other features, aspects, and advantages of the invention will be apparent to those skilled in the art from the following detailed description of preferred non-limiting exemplary embodiments, taken together with the drawings and the claims that follow.

BRIEF DESCRIPTION OF THE DRAWINGS

It is to be understood that the drawings are to be used for the purposes of exemplary illustration only and not as a definition of the limits of the invention. Throughout the disclosure, the word "exemplary" is used exclusively to mean "serving as an example, instance, or illustration." Any embodiment described as "exemplary" is not necessarily to be construed as preferred or advantageous over other embodiments.

Referring to the drawings in which like reference character(s) present corresponding part(s) throughout.

DETAILED DESCRIPTION OF THE INVENTION

The detailed description set forth below in connection with the appended drawings is intended as a description of presently preferred embodiments of the invention and is not intended to represent the only forms in which the present invention may be constructed and or utilized.

Figure 2A:
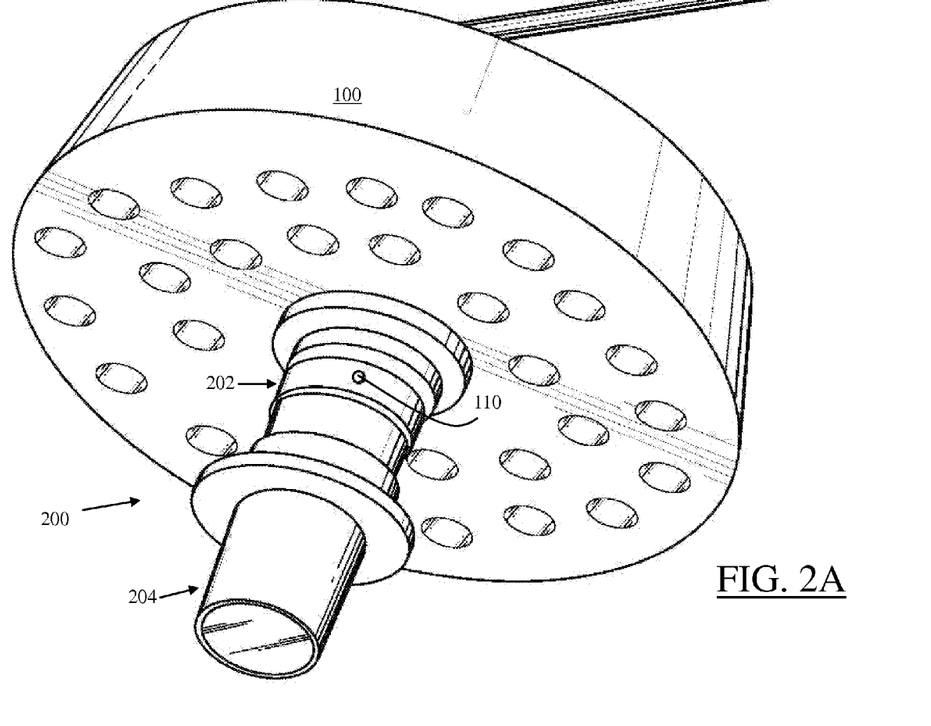
FIG. 2A is an illustration of an exemplary surgical camera mounted on a surgical light assembly that includes a surgical room camera replacement cover assembly in accordance with the present invention.
Figure 2B:
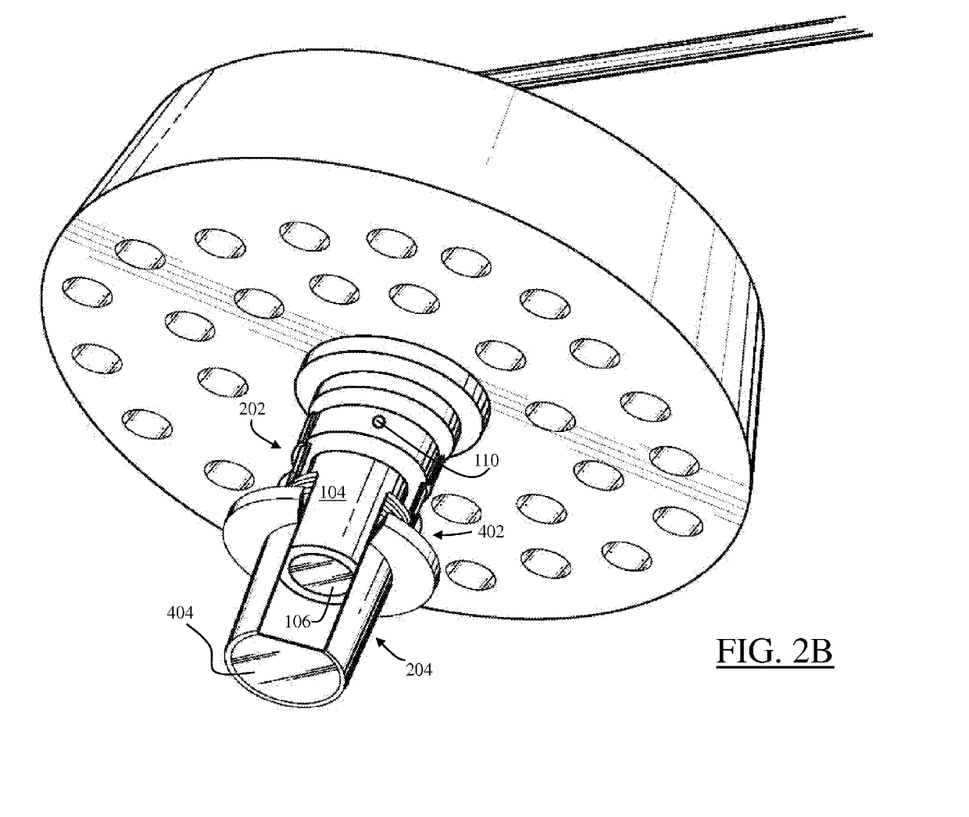
FIG. 2B is an exemplary sectional view illustration of the surgical room camera replacement cover assembly in accordance with the present invention.
Figure 3A:
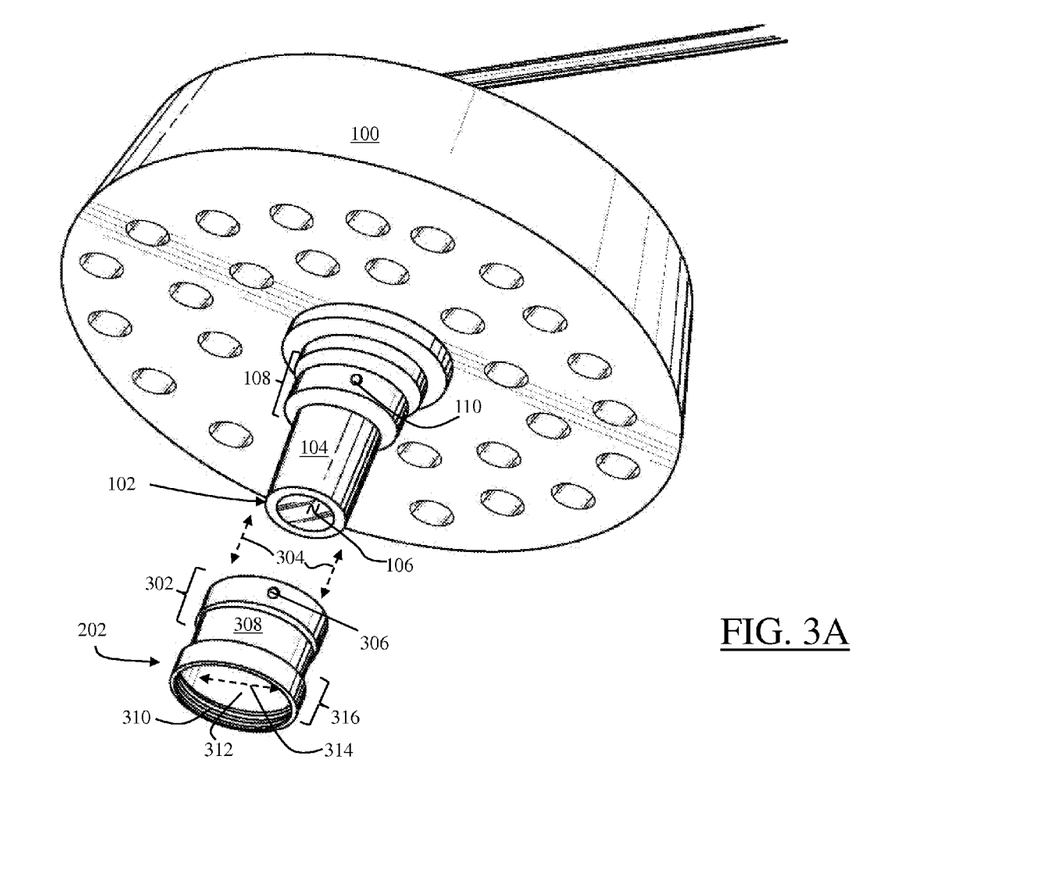
FIGS. 3A to 3F are illustrations of an exemplary universal adapter interface unit in accordance with the present invention.
Figure 3B:
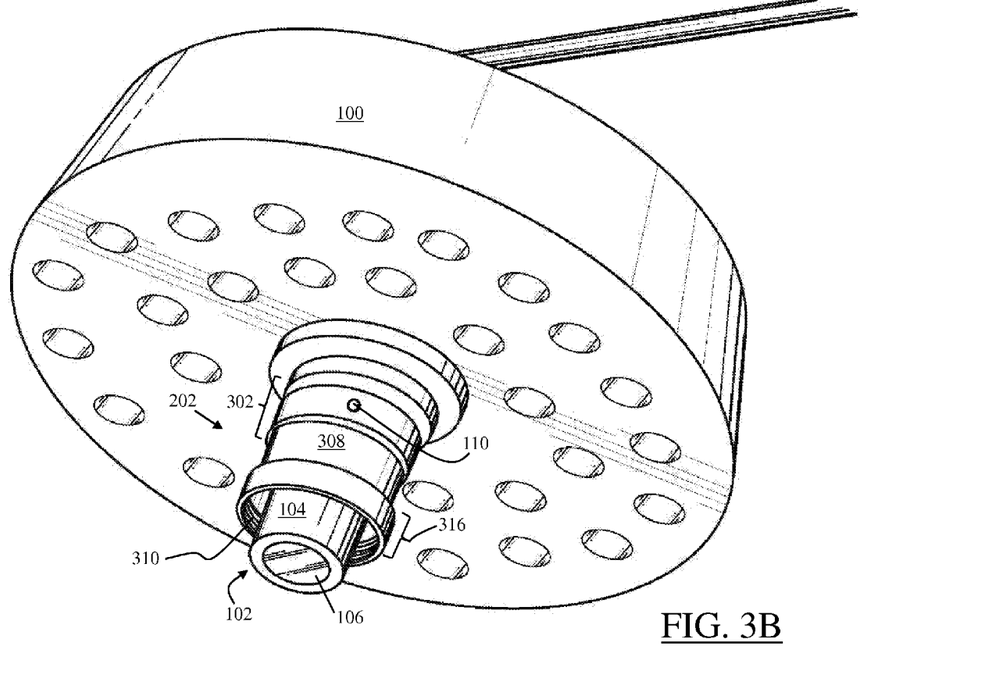
Figure 3C:
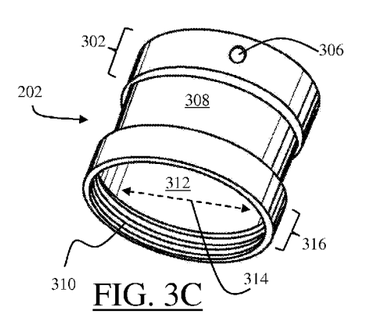
Figure 3D:
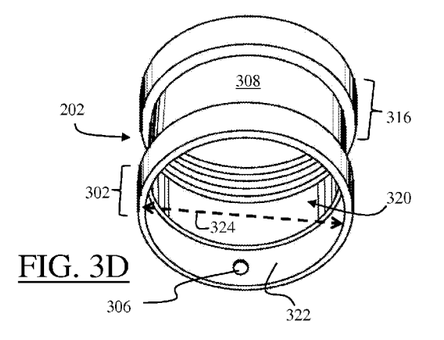
Figure 3E:
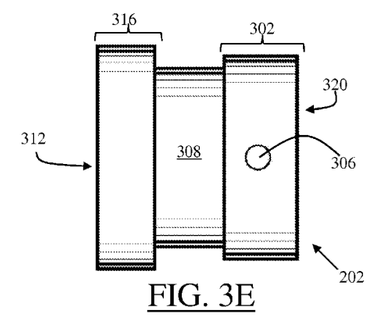
Figure 3F:
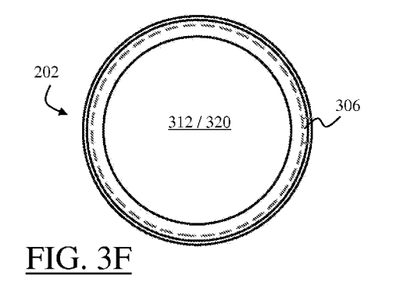

The present invention provides a sterile surgical room camera replacement cover assembly that is disposable, rigid, and universal. FIG. 2A is an illustration of an exemplary surgical camera mounted on a surgical light assembly that includes a surgical room camera replacement cover assembly in accordance with the present invention. FIG. 2B is a partially cut sectional view illustration of the surgical room camera replacement cover assembly in accordance with the present invention. As illustrated in FIGS. 2A and 2B, the present invention provides a surgical room camera replacement cover assembly 200 that includes a universal adapter interface unit 202 and a rigid, disposable, universal camera cover 204 that is detachably coupled with the universal adapter interface unit 202.

FIGS. 3A to 3F are illustrations of an exemplary universal adapter interface unit in accordance with the present invention. The universal adapter interface unit 202 includes a first section 302 (or the adapter section) that is specifically configured to detachably couple with a particular surgical light fixture 100, and a second section 316 (the universal section) that is configured to universally, detachably couple with the rigid, disposable, universal camera cover 204 in accordance with the present invention.

Before continuing further, it is very important to emphasize and understand that the drawings are to be used for the purposes of exemplary illustrations only and not in any way define the limits of the invention. For example, the drawings illustrate a very specific configuration of the first section 302 (the adapter section) of the universal adapter interface unit 202. That is, the first section 302 is specifically configured and particularly adapted to correspondingly match and to detachably couple with the correspondingly matched (i.e., complementary) connection section 108 of the specifically illustrated surgical light camera 102 of the surgical light fixture 100.

However, as stated above, all existing surgical light assemblies and their associated camera equipment are unique, specifically manufactured by competing companies. Of course, as a result of this wide variations in differences in surgical light assemblies and their respective camera equipment, it would not be practical and, in fact, impossible to illustrate all existing different surgical light assemblies and their uniquely associated camera equipment. Therefore, in the same respect, it would not be practical and, in fact, also impossible to illustrate all possible variations of the first section 302 (the adapter section) of the universal adapter interface unit 202 of the present invention that may be configured and adapted to correspondingly match with existing different surgical light assemblies and their associated camera equipment. Accordingly, the drawings shown are merely provided for illustrative purposes for better understanding of the present invention and should not be limiting to the specific surgical light fixture 100, surgical light camera 102, and its correspondingly matching first section 302 (the adapter section) of the universal adapter interface unit 202 of the present invention shown. For example, if the connection section 108 of the surgical light camera 102 is square, pentagon, or any other shape, then the first section 302 of the universal adapter interface unit 202 of the present invention may be configured and adapted to correspondingly match with the shape of the connection section 108 and fit to cover the surgical light camera 102. As another example, the connection section 108 of the surgical light camera 102 may have other fastening mechanisms such as a radial array of plurality of biased buttons instead of the single biasing button 110 that is illustrated. In such an exemplary instance, the first section 302 (the adapter section) of the universal adapter interface unit 202 of the present invention may be configured to include complementary, corresponding set of radial array of apertures to accommodate the radial array of plurality of biasing buttons to detachably couple the universal adapter interface unit 202 with the surgical light camera 102. In yet another instance, the connection section 108 of the surgical light camera 102 may use a snap on connection mechanism in which case, the first section 302 of the universal adapter interface unit 202 may comprise of snap on mechanism that snaps onto and detachably couples with the connection section 108 of the surgical light camera 102. Therefore, it is imperative to understand that the drawings are to be used for the purposes of exemplary illustrations only, and should in no way be limiting.

To continue, as further illustrated in FIGS. 3A to 3F, the first section 302 (the adapter section) of the universal adapter interface unit 202 includes an adapter mechanism (or coupling mechanism) that is configured to detachably couple with an associated fastening mechanism of a particular surgical light fixture. That is, the first section 302 (or the adapter section) is specifically configured and particularly adapted to associate with a specifically corresponding connection section of a particular surgical light camera. This enables coupling the universal adapter interface unit 202 with a particular surgical light fixture, but without modifying the surgical light fixture. Stated otherwise, the first section 302 of the universal adapter interface unit 202 of the present invention is configured and adapted to detachably couple with a surgical light fixture or camera in the same manner as any OEM camera cover is specifically and uniquely made to mate with its corresponding surgical light fixture or camera, but with no modifications to the surgical light fixture 100 or the surgical light camera 102.

Accordingly, with the abovementioned arrangement, multiple universal adapter interface units 202 with different types of first sections 302 (adapter sections) that are uniquely configured and specifically adapted for detachable connection with different surgical light fixtures would be required. This would be particularly true for a hospital having multiple different types of surgical light assemblies (including the uniquely associated surgical light camera) from multiple manufacturing companies.

As further illustrated, the second section 316 (the universal section) of the universal adapter interface unit 202 includes a fastener 310 that detachably couples with the rigid, disposable, universal camera cover 204. Different variations of fasteners are possible, and should not be limiting to the illustrated threaded section 310. The second section 316 (or the universal section) with the fastener 310 enables a true camera cover (and not just an accessory or a soft cover) to couple with the surgical light fixture via the universal adapter interface unit 202. This way, the OEM cover is no longer needed, and instead, the rigid, disposable, universal camera cover 204 of the present invention is used, and disposed of after a single use. This can potentially lower costs and improve efficiency of operating room use. Of course, the rigid, disposable, universal camera cover 204 of the present invention is sterilized before it is used, packaged, and then disposed of after use. Please note that the universal adapter interface unit 202 need not be sterilized for it is generally considered as part of non-sterile field or zone of an operating room.

As further illustrated in FIGS. 3A to 3F, in this exemplary instance, the first section 302 (or the adapter mechanism) of universal adapter interface unit 202 is configured to include an aperture 306 that accommodates the exemplary biasing button 110 of the surgical light camera 102. The universal adapter interface unit 202 is first placed on the surgical light camera 102 by maneuvering it along the path 304 and orienting the aperture 306 to align with the biasing button 110. When fully inserted onto the surgical light camera 102 (illustrated in FIG. 3B), the biasing button snaps into the aperture 306 of the first section 302 of the universal adapter interface unit 202, locking the universal adapter interface unit 202 on the surgical light camera 102. As further illustrated, the first section 302 of the universal adapter interface unit 202 includes a first opening 320 with a diameter 324, an inner contour 322, and the aperture 306 that is exactly configured to detachably fit onto and mate with the connection section 108 of the surgical light camera 102. The universal adapter interface unit 202 further includes a mid-section 308 that may be of any reasonable length and shape, but with a cross-sectional distance (e.g., diameter) that enables the universal adapter interface unit 202 to clear and mate onto the surgical light camera 102.

As further illustrated, universal adapter interface unit 202 also includes the second section 316 (the universal section) that is configured to universally, detachably couple with the substantially rigid, disposable, universal camera cover 204 of the present invention. The second section 316 of the universal adapter interface unit 202 includes a second opening 312 with a diameter 314, and a second inner contour 310 that is threaded. It should be noted that the configurations of the first section 302 (adapter section) and the second section 316 (universal section) are independent of one another. That is, the first section 302 (adapter section) is specifically configured to mate with a corresponding connection section of a surgical light camera and may comprise of any shape or diameter (or cross-sectional length). On the other hand, the second section 316 (the universal section) of the universal adapter interface unit 202 is configured to mate with the rigid, disposable, universal camera cover 204 of the present invention with its own unique connection characteristics (the details of which are provided below).

Figure 4A:
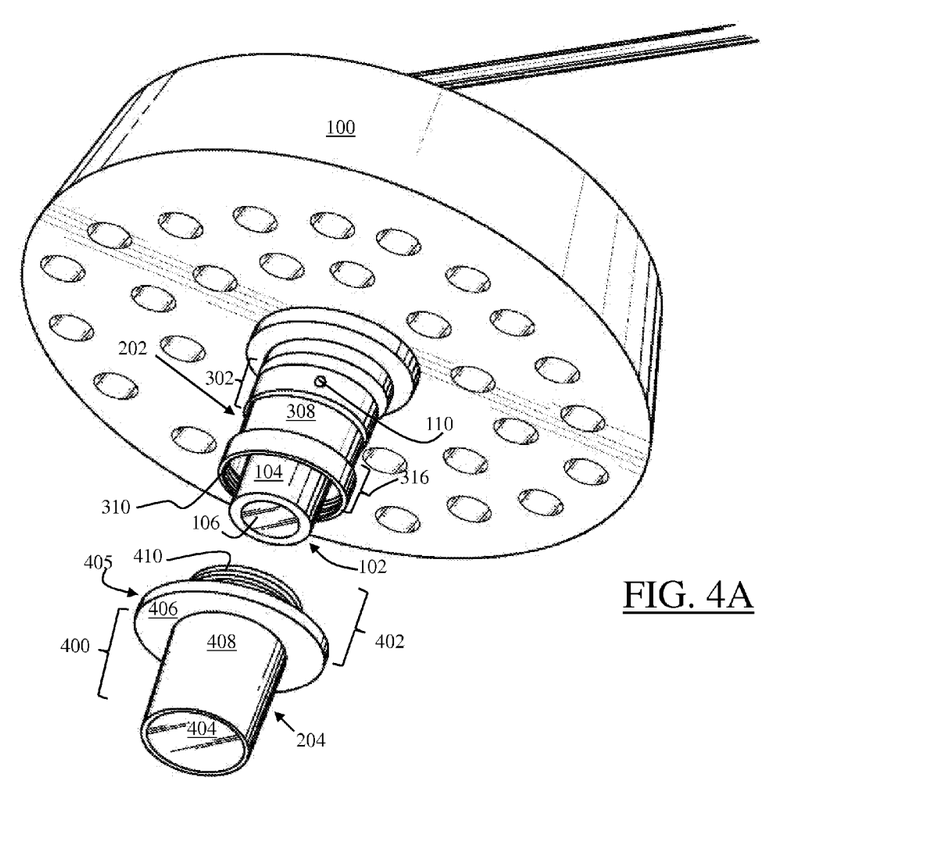
FIG. 4A is an illustration of an exemplary rigid, disposable, universal camera cover and the universal adapter interface unit in accordance with the present invention.
Figure 4B:
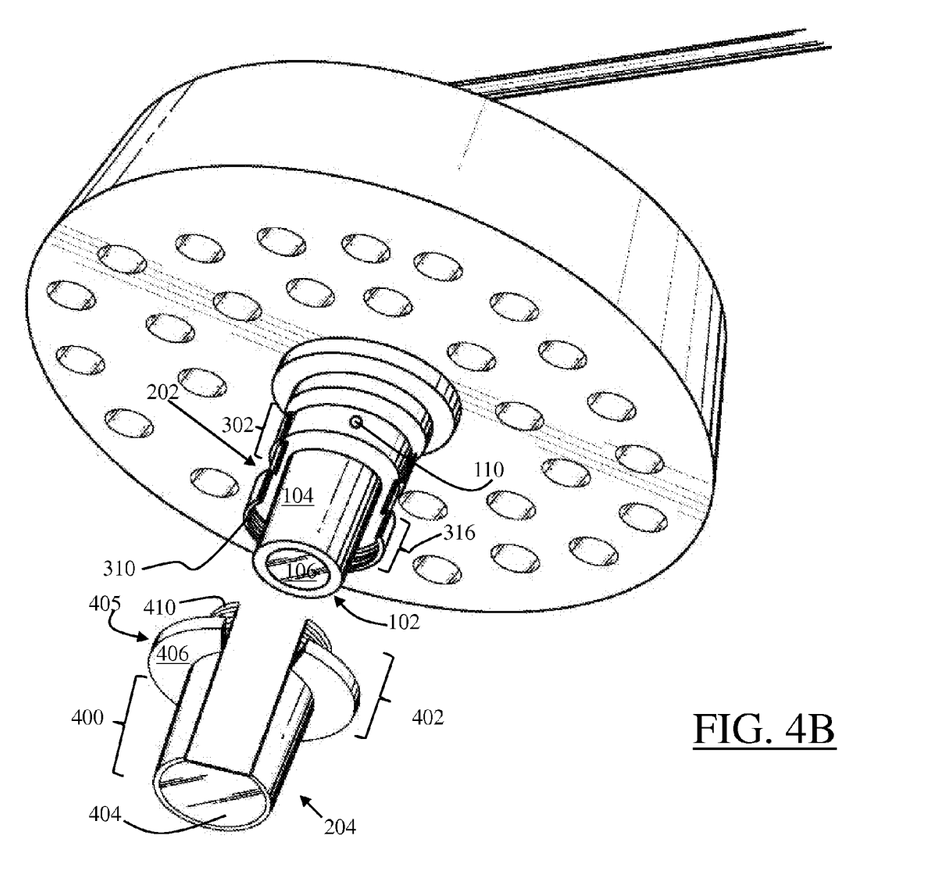
FIG. 4B is an illustration of an exemplary perspective sectional view of the combined rigid, disposable, universal camera cover and the universal adapter interface unit in accordance with the present invention.
Figure 4C:
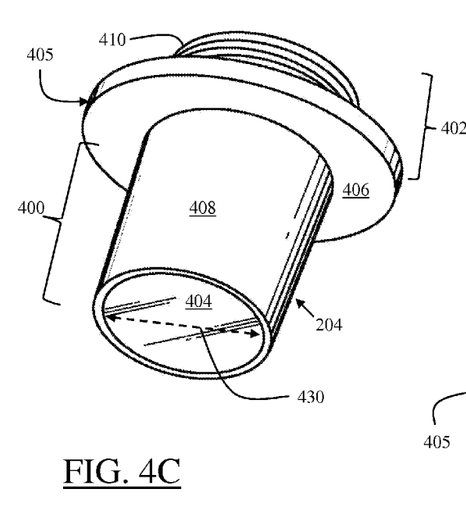
FIGS. 4C to 4F are various illustrative views of an exemplary rigid, disposable, universal camera cover in accordance with the present invention.
Figure 4D:
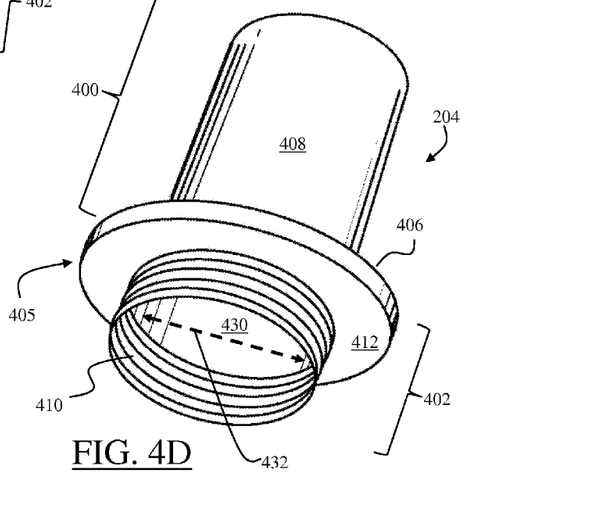
Figure 4E:
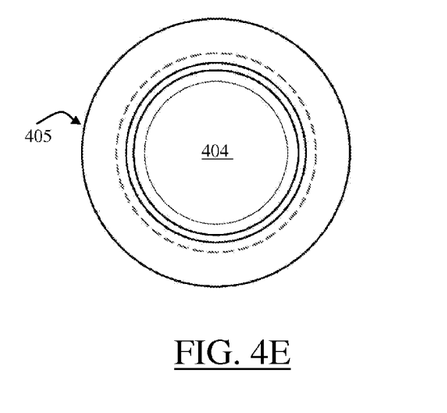
Figure 4F:
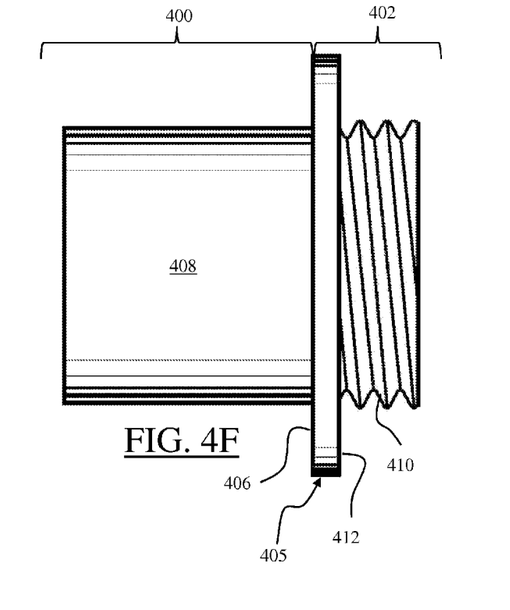

FIG. 4A is an illustration of an exemplary rigid, disposable, universal camera cover and the universal adapter interface unit in accordance with the present invention. FIG. 4B is an illustration of an exemplary perspective sectional view of the combined rigid, disposable, universal camera cover and the universal adapter interface unit in accordance with the present invention. FIGS. 4C to 4F are various illustrative views of an exemplary rigid, disposable, universal camera cover in accordance with the present invention. As illustrated in FIGS. 4A to 4F, the rigid, disposable, universal camera cover 204 is generally comprised of molded plastic, and includes a lower section 400 that generally falls within the sterile field of an operating room, and an upper section 402 that is within the non-sterile field of an operating room. The lower section 400 of the rigid, disposable, universal camera cover 204 includes a viewing section 404 that provides a view of an operative field for the surgical light camera equipment 102. The viewing section 404 is transparent, and is comprised of material that can withstand the rigors of sterilization, non-limiting examples of which may include a gamma stable acrylic material. Diameter 430 of the viewing section 404 may be of any span so long as it does not block the view of the camera lens 106.

As further illustrated, the lower section 400 of the rigid, disposable, universal camera cover 204 of the present invention further includes a body 408 that houses and provides a sterile, protective covering for the camera equipment 102. In this exemplary instance, the body 408 is exemplarily configured as substantially cylindrical, with sufficient height and diameter to enable insertion and full coverage of the surgical light camera 102. The rigid, disposable, universal camera cover 204 of the present invention must be of sufficient thickness to be sturdy. It is imperative to note that the lower section 400 of the rigid, disposable, universal camera cover 204 of the present invention may be of any shape and size, and should not be limited to the illustrated cylindrical configuration shown, so long as the rigid, disposable, universal camera cover 204 of the present invention fully covers the more expensive and costly surgical light camera 102. Accordingly, any cross-section configuration with any cross-sectional length with sufficient span that would not block the view of the camera lens 106 and would allow the surgical light camera 102 to fit within the body 408 may be used. For example, the body 408 may comprise of a cone structure with a wider top (near the flange 405) or wider bottom (near the viewing section 404). Accordingly, the rigid, disposable, universal camera cover 204 of the present invention should not be limited to the illustrated right-cylindrical configuration with a substantially uniform circular cross-section along the height of the body 408. In addition, the height of the rigid, disposable, universal camera cover 204 may also vary to accommodate any height surgical light camera.

As further illustrated, included with the rigid, disposable, universal camera cover 204 is a sterile barrier 405 (i.e., flange) in the form a radial flange that limits a grip of a user to within a sterile field. The overall diameter of the radial flange (that constitutes the sterile barrier 405) must be of sufficient span to provide a stop for the hand grip, and prevent and block the hand of the user to pass or move into the non-sterile field (or the upper section 402). That sterile barrier 405 includes a first side 406 that is within the sterile field section 400 and a second side 412 that faces the non-sterile field section 402.

As further illustrated, the substantially rigid, disposable, universal camera cover 204 further includes the upper section 402, which has a universal coupling section 410 that couples the rigid, disposable, universal camera cover 204 with the second section 316 of the universal adapter interface unit 202 that includes a fastener 310. The height of the upper section 402 may be varied, depending on the type of fastener system used to detachably couple the rigid, disposable, universal camera cover 204 with the universal adapter interface unit 202. For example, instead of male threaded section 410 coupled with a female threaded section 310, the fastener or coupling system may be a snap-on type. That is, one of the universal fastener 310 or the universal coupling section 410 may have a protrusion that snaps into a complimentary indentation of the other. Accordingly, any type of connection mechanism that enables the rigid, disposable, universal camera cover 204 to detachably couple with the universal adapter interface unit 202 may be used, and should not be limited to the illustrated threaded scheme. Further, the cross-sectional span 432 of the top opening 430 of the rigid, disposable, universal camera cover 204 should be commensurate with the associated universal adapter interface unit 202 with which it is detachably coupled.

Although the invention has been described in considerable detail in language specific to structural features and or method acts, it is to be understood that the invention defined in the appended claims is not necessarily limited to the specific features or acts described. Rather, the specific features and acts are disclosed as preferred forms of implementing the claimed invention. Stated otherwise, it is to be understood that the phraseology and terminology employed herein, as well as the abstract, are for the purpose of description and should not be regarded as limiting. Therefore, while exemplary illustrative embodiments of the invention have been described, numerous variations and alternative embodiments will occur to those skilled in the art, a few of which are mentioned above. Such variations and alternate embodiments are contemplated, and can be made without departing from the spirit and scope of the invention.

It should further be noted that throughout the entire disclosure, the labels such as left, right, front, back, top, bottom, forward, reverse, clockwise, counter clockwise, up, down, or other similar terms such as upper, lower, aft, fore, vertical, horizontal, oblique, proximal, distal, parallel, perpendicular, transverse, longitudinal, etc. have been used for convenience purposes only and are not intended to imply any particular fixed direction or orientation. Instead, they are used to reflect relative locations and/or directions/orientations between various portions of an object.

In addition, reference to "first," "second," "third," and etc. members throughout the disclosure (and in particular, claims) is not used to show a serial or numerical limitation but instead is used to distinguish or identify the various members of the group.

In addition, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of," "act of," "operation of," or "operational act of" in the claims herein is not intended to invoke the provisions of 35 U.S.C. 112, Paragraph 6.

What is claimed is:

1. A replacement cover assembly, comprising:
a separate and independent universal adapter interface unit;
the separate and independent universal adapter interface unit independently and directly couples with a surgical camera equipment of the operating room surgical lamp lighting fixture;
the separate and independent universal adapter interface unit includes:
an adapter body with a hollow interior defined by a through-hole along a longitudinal axis of the universal adapter interface unit with sufficient cross-sectional span for allowing passage of the surgical camera equipment of the operating room surgical lamp lighting fixture through the hollow interior, enabling the universal adapter interface unit to maneuver over the surgical camera equipment to couple with the surgical camera equipment of the operating room surgical lamp lighting fixture;

the adapter body includes:
an adaptor section that has a fastener that is specifically configured and particularly adapted to correspondingly match and to detachably couple with a correspondingly matched, complementary connection section of the surgical camera equipment of the operating room surgical lamp lighting fixture; and
a universal section that is configured to universally, detachably couple directly with a separate and independent, substantially rigid, disposable, universal camera cover;
the substantially rigid, disposable, universal camera cover is separate from and independent of the universal adaptor interface unit, the surgical camera equipment of the operating room surgical lamp lighting fixture, and the operating room surgical lamp lighting fixture and includes:
a lower section that substantially falls within a sterile field of an operating room environment, and includes:
a viewing section with a transparent cover that provides a view of an operative field for the surgical camera equipment of the operating room surgical lamp lighting fixture;
a hollow body with sufficient cross-sectional span and height that houses and provides a sterile, full protective covering for the surgical camera equipment of the operating room surgical lamp lighting fixture;
a first side of a barrier that limits a grip of a user to within a sterile field when moving the operating room surgical lamp lighting fixture;
the barrier is comprised of:
a radial flange of sufficient span to prevent and block a hand of the user to move beyond the sterile field; and
the independent and separate, substantially rigid, disposable, universal camera cover further includes:
an upper section that substantially falls within a non-sterile field of the operating room environment, and includes:
a second side of the barrier; and
a universal coupling section that directly, mechanically couples the separate and independent, substantially rigid, disposable, universal camera cover with the universal section of the universal adapter interface unit that includes a universal fastener.

2. A replacement cover assembly, comprising:
a separate and independent universal adapter interface unit:
that includes an adapter body with a hollow interior defined by a through-hole with sufficient cross-sectional span for allowing maneuvering of the universal adapter interface unit over an operating room surgical lamp lighting fixture camera equipment through the hollow interior;
the adapter body includes:
an adaptor section specifically configured and particularly adapted to correspondingly match and to detachably couple with a correspondingly matched, complementary connection section of the operating room surgical lamp lighting fixture camera equipment;
a universal section that is configured to universally, detachably directly couple with a separate and independent substantially rigid, disposable, universal camera cover;
the substantially rigid, disposable, universal camera cover includes:
a lower section that substantially falls within a sterile field of an operating room environment, and an upper section that substantially falls within a non-sterile field of the operating room environment;
a viewing section within the lower section with a transparent cover that provides a view of an operative field for the operating room surgical lamp lighting fixture camera equipment;
a hollow body within the lower section with sufficient cross-sectional span and height that houses and provides a sterile, full protective covering for the camera equipment;
a barrier in between the lower and upper sections that limits a grip of a user to within a sterile field when moving the operating room surgical lamp lighting fixture;
the barrier is comprised of:
a flange of sufficient span to prevent and block a hand of the user to move beyond the sterile field; and
a universal coupling section within the upper section that directly and mechanically couples the substantially rigid, disposable, universal camera cover with the universal section of the universal adapter interface unit that includes a universal fastener.

* * * * *